(12) United States Patent
Chen

(10) Patent No.: US 9,655,598 B2
(45) Date of Patent: May 23, 2017

(54) SAMPLING APPARATUS

(71) Applicant: Chien-Liang Chen, Taichung (TW)

(72) Inventor: Chien-Liang Chen, Taichung (TW)

(\*) Notice: Subject to any disclaimer, the term of this patent is extended or adjusted under 35 U.S.C. 154(b) by 430 days.

(21) Appl. No.: 14/335,975

(22) Filed: Jul. 21, 2014

(65) Prior Publication Data
US 2016/0015371 A1    Jan. 21, 2016

(51) Int. Cl.
*A61B 10/00*    (2006.01)
*A61B 10/02*    (2006.01)

(52) U.S. Cl.
CPC .. *A61B 10/0266* (2013.01); *A61B 2010/0208* (2013.01); *A61B 2560/0418* (2013.01)

(58) Field of Classification Search
CPC ............ A61B 10/0275; A61B 10/0266; A61B 2010/0208
USPC .......................................................... 600/567
See application file for complete search history.

(56) References Cited

U.S. PATENT DOCUMENTS

| | | | | |
|---|---|---|---|---|
| 4,438,566 | A * | 3/1984 | Sakata ...................... | G01B 5/12 33/501.2 |
| 2002/0064886 | A1* | 5/2002 | Nakagawa ............... | G01N 1/04 436/177 |
| 2006/0213029 | A1* | 9/2006 | Lu ......................... | A45C 13/262 16/113.1 |
| 2007/0110617 | A1* | 5/2007 | Nagai .................. | G01N 35/026 422/65 |
| 2011/0116971 | A1* | 5/2011 | Nagai ................. | B01F 11/0008 422/68.1 |
| 2011/0130681 | A1* | 6/2011 | Okumura ........... | A61B 10/0038 600/573 |
| 2015/0246436 | A1* | 9/2015 | Huang .................. | B25B 27/023 29/256 |

\* cited by examiner

*Primary Examiner* — Daniel Cerioni
(74) *Attorney, Agent, or Firm* — Alan D. Kamrath; Kamrath IP Lawfirm, P.A.

(57) ABSTRACT

A sampling apparatus contains: a tubular member, a pressing mechanism, a forcing member, and a movable sampling member. The tubular member includes an inner thread section, an orifice, a stepped shoulder, a first fixing hole, and a second fixing hole. The pressing mechanism includes a press member, a driving member, a resilient element, and an elastic hook. The driving member includes an inserting segment, an aperture, a retaining slot, and a receiving groove, and two ends of the resilient element abut against the driving member and the forcing member. The cylindrical member includes an outer thread section and two opposite positioning recesses. The forcing member includes a needle and two opposite locating stems. The movable sampling member includes a hollowly lower side, a hollow affixing mount, a hollow tool, and a blade.

3 Claims, 9 Drawing Sheets

FIG·1

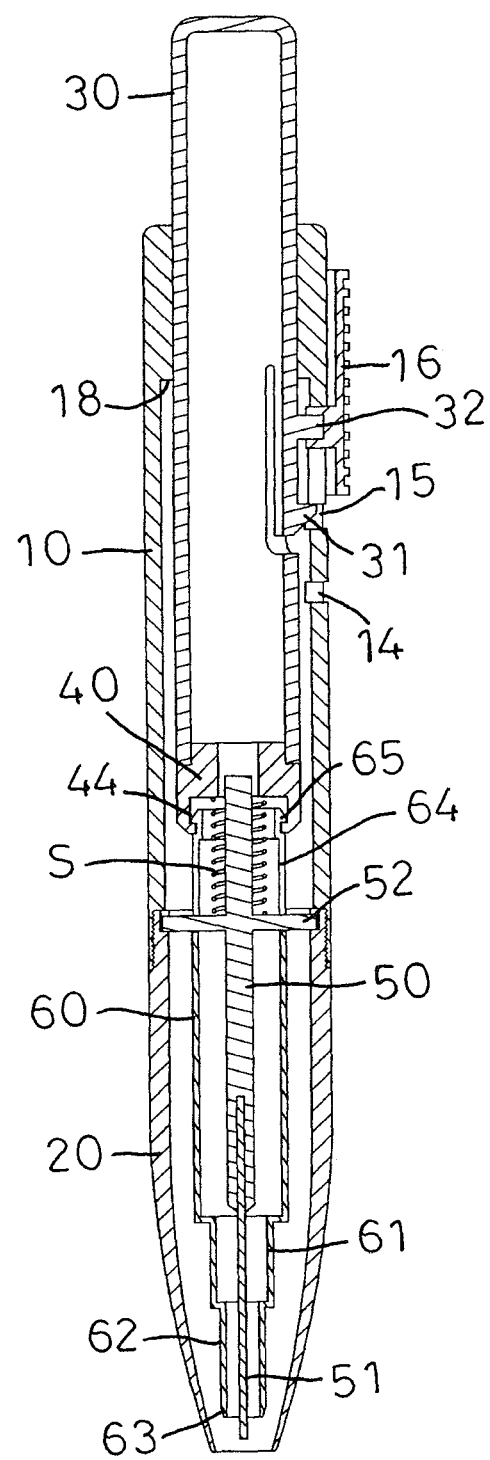
FIG · 3

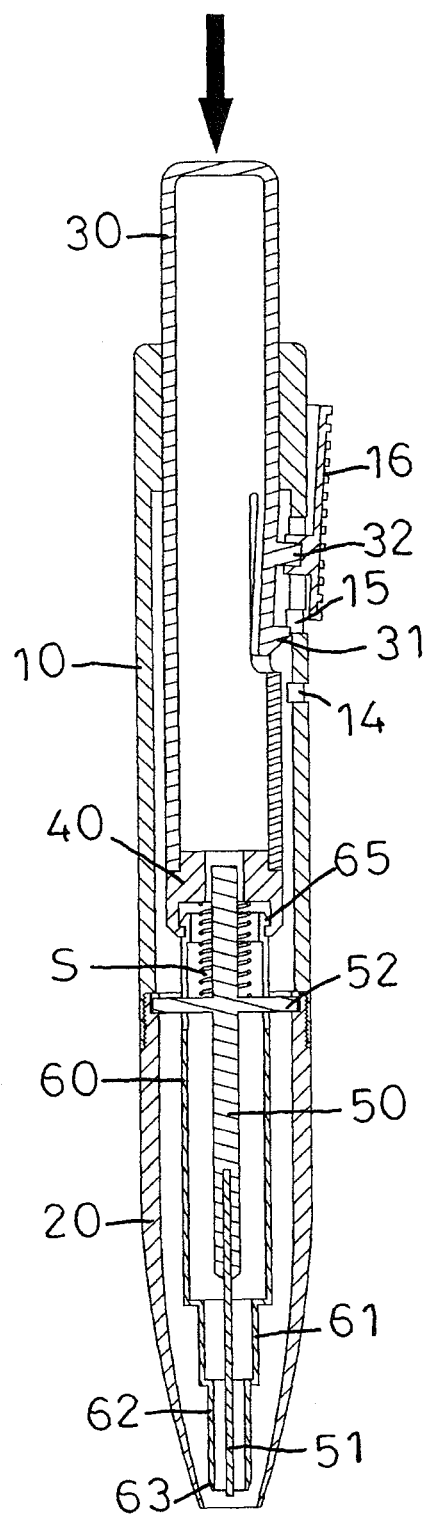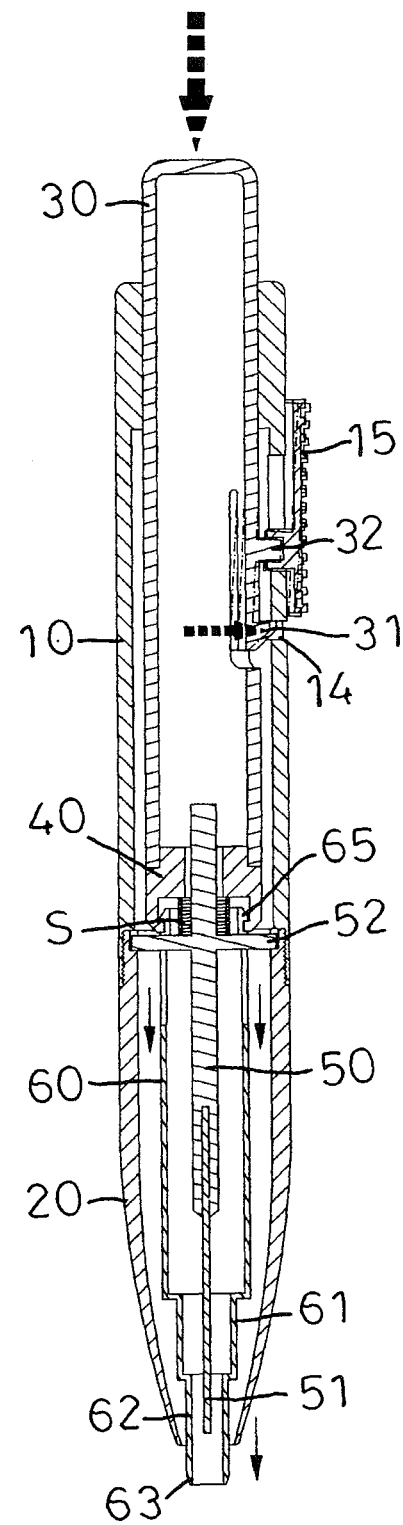
FIG·4　　　FIG·5

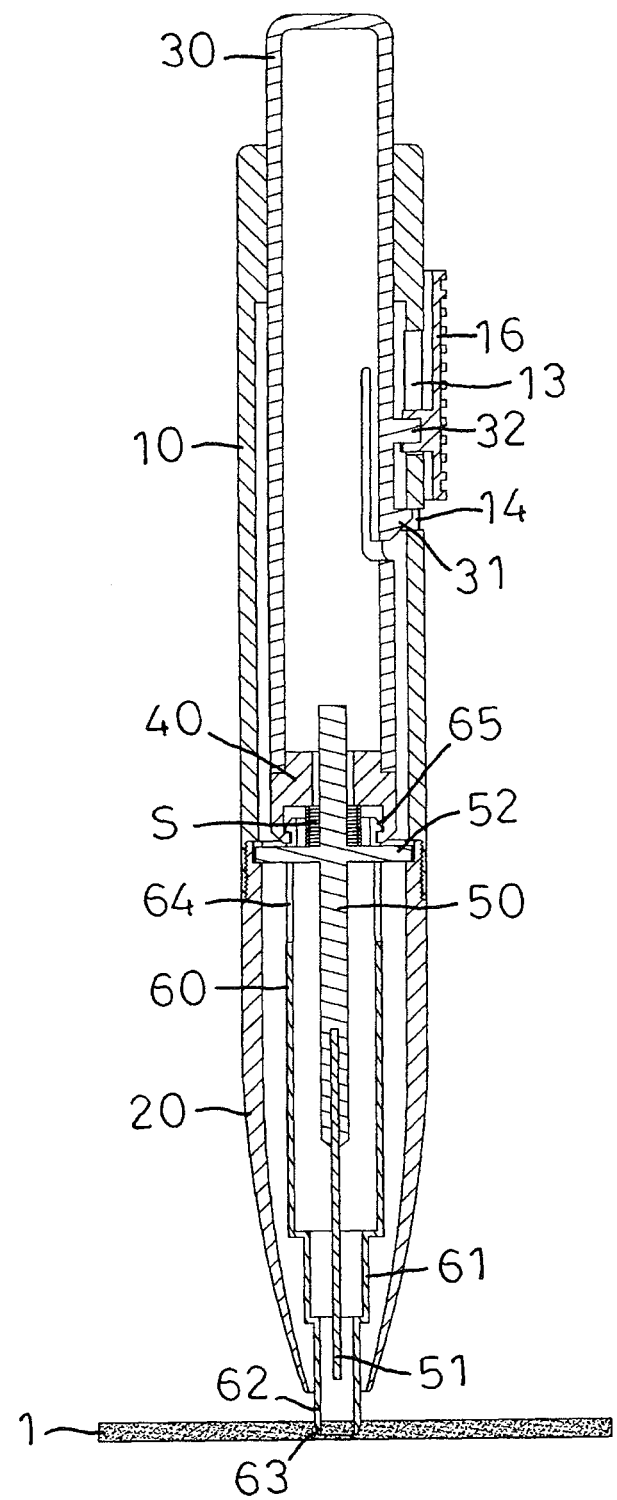
FIG·6

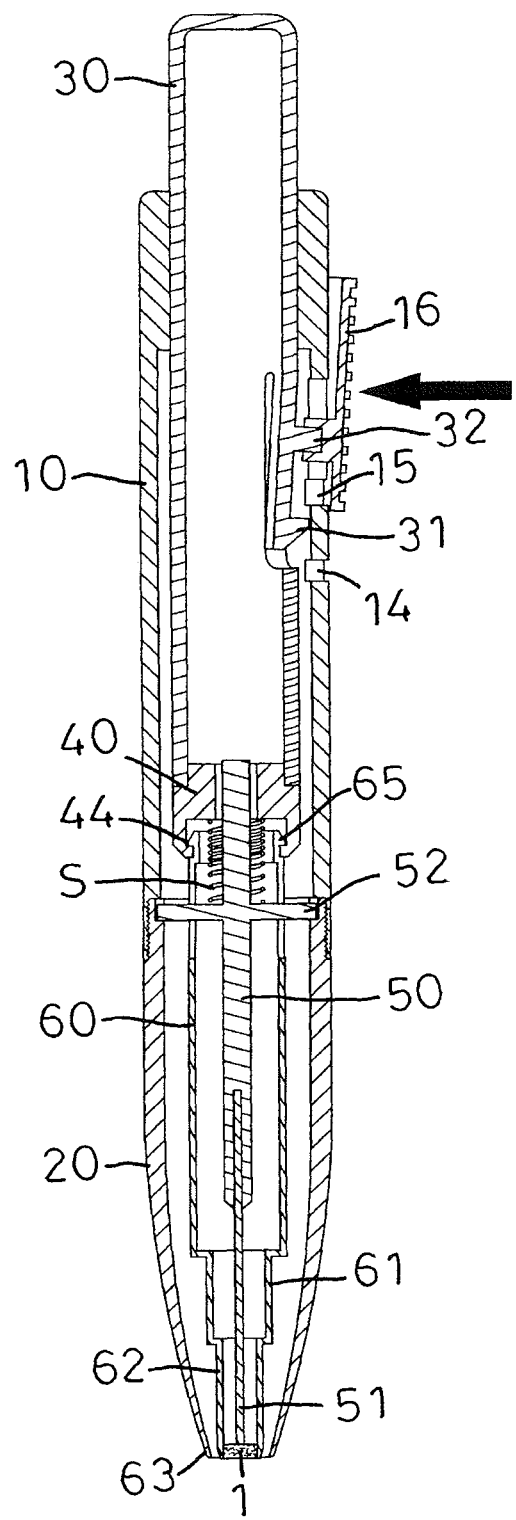
FIG·7

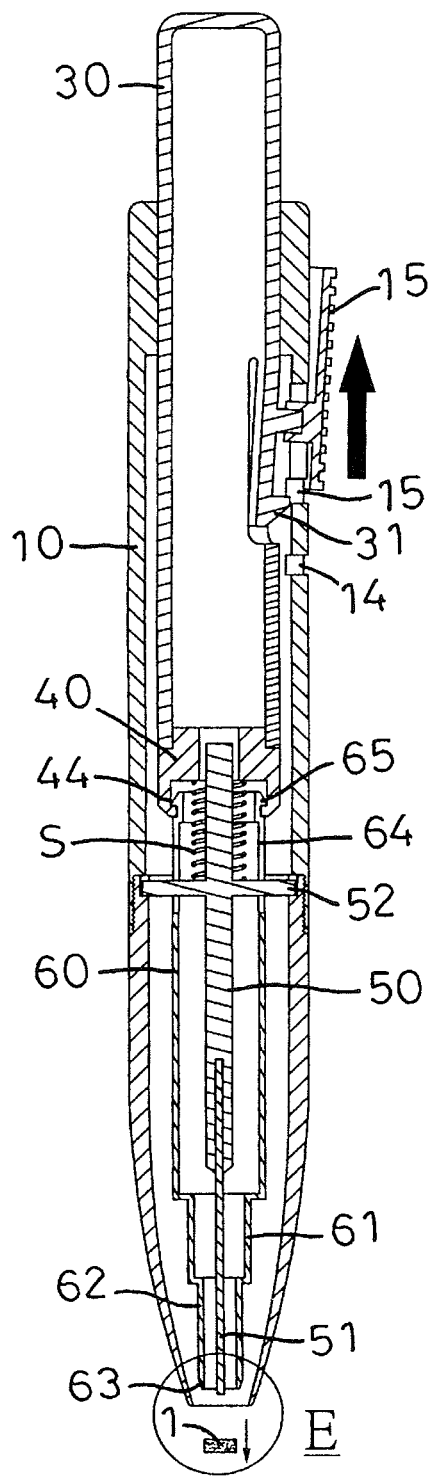
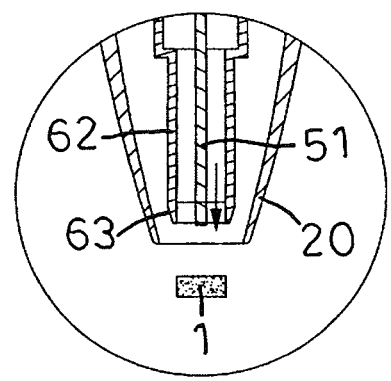
FIG·9
FIG·8

SAMPLING APPARATUS

FIELD OF THE INVENTION

The present invention relates to a sampling apparatus which extends and retracts a tool easily.

BACKGROUND OF THE INVENTION

A conventional sampling apparatus contains: a hollowly cylindrical head with an opening defined on a tip end thereof, a plunger longitudinally moving in the hollowly cylindrical head, and a tubular distal segment, wherein the tip end of the hollowly cylindrical head is employed to cut a sample, and the tubular distal segment is removably fixed on the hollowly cylindrical head.

However, the tip end cannot be retracted into the sampling apparatus, thus injuring user and having infection.

The present invention has arisen to mitigate and/or obviate the afore-described disadvantages.

SUMMARY OF THE INVENTION

The primary objective of the present invention is to provide a sampling apparatus which retracts a tool into a cylindrical member to obtain safety and hygiene, when the sampling apparatus is not in use.

BRIEF DESCRIPTION OF THE DRAWINGS

FIG. 3 is a cross sectional view showing the assembly of the sampling apparatus according to the first embodiment of the present invention.

FIG. 4 is a cross sectional view showing the operation of a press member of the sampling apparatus according to the first embodiment of the present invention.

FIG. 5 is a cross sectional view showing the operation of a movable sampling member of the sampling apparatus according to the first embodiment of the present invention.

FIG. 6 is a cross sectional view showing the application of the sampling apparatus according to the first embodiment of the present invention.

FIG. 7 is a cross sectional view showing the operation of a pushing block of the sampling apparatus according to the first embodiment of the present invention.

FIG. 8 is a cross sectional view showing a movable sampling member pushing a sample outwardly according to the first embodiment of the present invention.

FIG. 9 is an amplified cross sectional view of a portion E of FIG. 8.

DETAILED DESCRIPTION OF THE PREFERRED EMBODIMENTS

Figure 1:
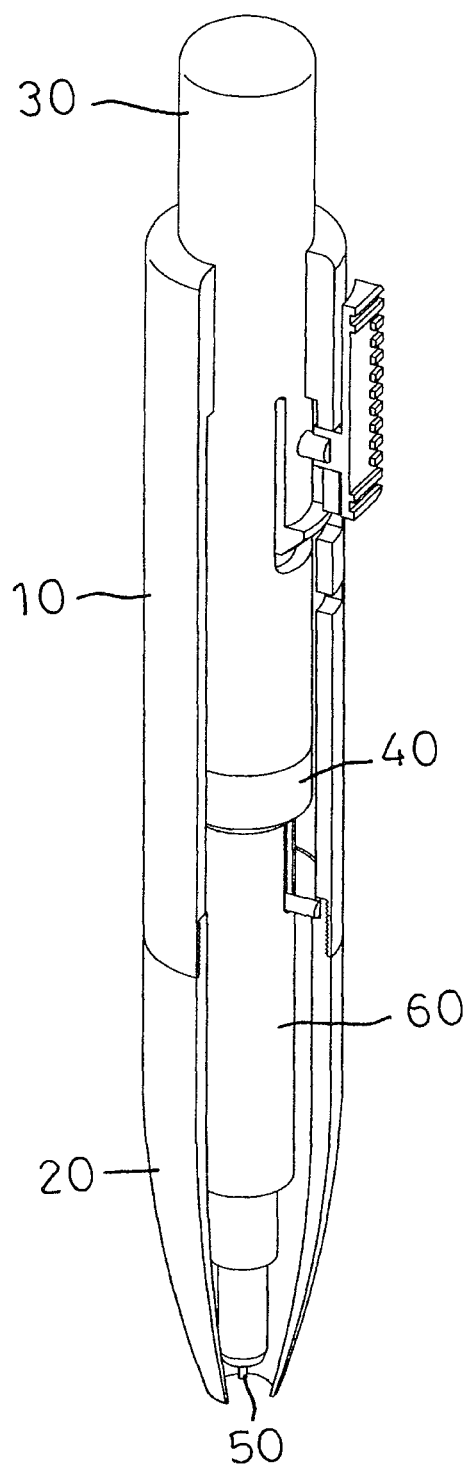
FIG. 1 is a perspective view showing the assembly of a sampling apparatus according to a first embodiment of the present invention.
Figure 2:
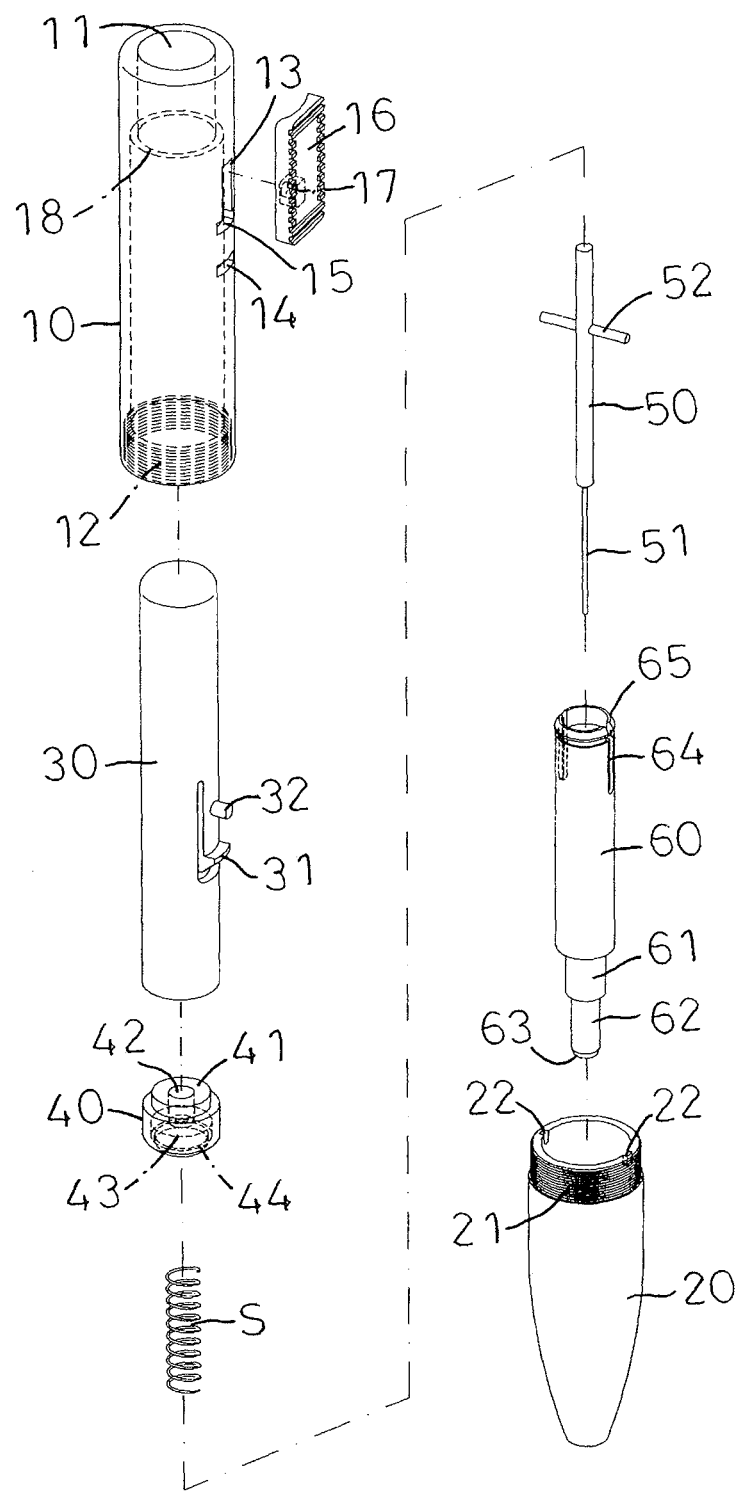
FIG. 2 is a perspective view showing the exploded components of the sampling apparatus according to the first embodiment of the present invention.

FIG. 1 is a perspective view showing the assembly of a sampling apparatus according to a first embodiment of the present invention. FIG. 2 is a perspective view showing the exploded components of the sampling apparatus according to the first embodiment of the present invention. FIG. 3 is a cross sectional view showing the assembly of the sampling apparatus according to the first embodiment of the present invention. The sampling apparatus comprises a tubular member 10, a cylindrical member 20, a pressing mechanism (including a press member 30, a driving member 40, and a resilient element S), a forcing member 50, and a movable sampling member 60.

The tubular member 10 includes an orifice 11 defined on a central position of an upper side thereof to insert the press member 30, an inner thread section 12 defined around a lower side of an inner wall thereof to screw with the cylindrical member 20. The tubular member 10 is hollow so as to accommodate the pressing mechanism (including the press member 30, the driving member 40, and the resilient element S) and also includes a first fixing hole 14, a second fixing hole 15, and a longitudinal hole 13 which are vertically arranged on an outer wall of the tubular member 10. The tubular member 10 further includes a pushing block 16 disposed outside the longitudinal hole 13 and includes a fitting seat 17 arranged in the pushing block 16 to correspond to the longitudinal hole 13, such that the pushing block 16 slides upwardly or downwardly in the longitudinal hole 13 by ways of the fitting seat 17, and the fitting seat 17 is fitted with the press member 30. The tubular member 10 further includes a stepped shoulder 18 formed around an upper side of the inner wall thereof to prevent the pressing mechanism (including the press member 30, the driving member 40, and the resilient element S) from removal.

The cylindrical member 20 includes an outer thread section 21 arranged around an upper side of an outer wall thereof to screw with the inner thread section 12 of the tubular member 10, and the cylindrical member 20 also includes two opposite positioning recesses 22 defined on a top end thereof.

The press member 30 extends out of an upper end of the orifice 11 from a bottom end of the tubular member 10 and includes an elastic hook 31 fixed on an outer wall thereof to alternatively hook with the first fixing hole 14 and the second fixing hole 15, and the press member 30 also includes a coupling post 32 extending outwardly from the outer wall thereof above the elastic hook 31 to fit into the fitting seat 17 of the pushing block 16.

The driving member 40 includes an inserting segment 41 formed on an upper side thereof and inserted into a lower side of the press member 30, an aperture 42 defined on a central position of the inserting segment 41 to insert the forcing member 50, and a receiving groove 43 formed in a lower side thereof to accommodate the resilient element S, wherein a first end of the resilient element S abuts against the receiving groove 43 of the driving member 40. The driving member 40 also includes a retaining slot 44 defined on the inner wall thereof below the receiving groove 43 to retain with the movable sampling member 60.

The forcing member 50 includes a needle 51 fixed on a bottom end thereof and two opposite locating stems 52 extending outwardly from an upper side thereof to correspond to the two opposite positioning recesses 22 of the cylindrical member 20, such that when the cylindrical member 20 is locked in the tubular member 10, the two opposite locating stems 52 are mounted in the two opposite positioning recesses 22 of the cylindrical member 20 so that the forcing member 50 is fixed, and a second end of the resilient element S is biased against the two opposite locating stems 52 of the forcing member 50.

The movable sampling member 60 includes a hollowly lower side, a hollow affixing mount 61 and a hollow tool 62 which are both one piece formed with the hollowly lower side, the movable sampling member 60 also includes a blade 63 arranged on a distal end of the tool 62 to cut a sample and includes two opposite trenches 64 defined on an upper side thereof to correspond to the two opposite locating stems 52 of the forcing member 50, such that when the movable sampling member 60 extends outwardly or retracts inwardly, it shirks the two opposite locating stems 52, and when the movable sampling member 60 retracts into the cylindrical member 20, the needle 51 exposes outside the blade 63 slightly. In addition, the movable sampling member 60 further includes a locking rib 65 arranged around a top end of the upper side thereof to retain with the retaining slot 44 of the driving member 40.

FIG. 4 is a cross sectional view showing the operation of the press member of the sampling apparatus according to the first embodiment of the present invention. FIG. 5 is a cross sectional view showing the operation of the movable sampling member of the sampling apparatus according to the first embodiment of the present invention. When the press member 30 is pressed downwardly, the elastic hook 31 of the press member 30 hooks with the first fixing hole 14 of the tubular member 10, and the resilient element S is pressed to generate an upward returning elasticity, such that the tool 62 of the movable sampling member 60 extends out of the cylindrical member 20 to expose the blade 63.

FIG. 6 is a cross sectional view showing the application of the sampling apparatus according to the first embodiment of the present invention. The blade 63 of the tool 62 is applied to cut and sample the sample 1.

FIG. 7 is a cross sectional view showing the operation of the pushing block of the sampling apparatus according to the first embodiment of the present invention. After sampling the sample 1, the pushing member 16 is pressed so that the elastic hook 31 of the press member 30 removes from the first fixing hole 14.

FIG. 8 is a cross sectional view showing the movable sampling member pushing the sample outwardly according to the first embodiment of the present invention. FIG. 9 is an amplified cross sectional view of a portion E of FIG. 8. The resilient element S pushes the elastic hook 31 of the press member 30 upwardly to hook in the second fixing hole 15 of the tubular member 10, the tool 62 of the movable sampling member 60 retracts into the cylindrical member 20, and the needle 51 of the forcing member 50 pushes the sample 1 outwardly.

Figure 10:
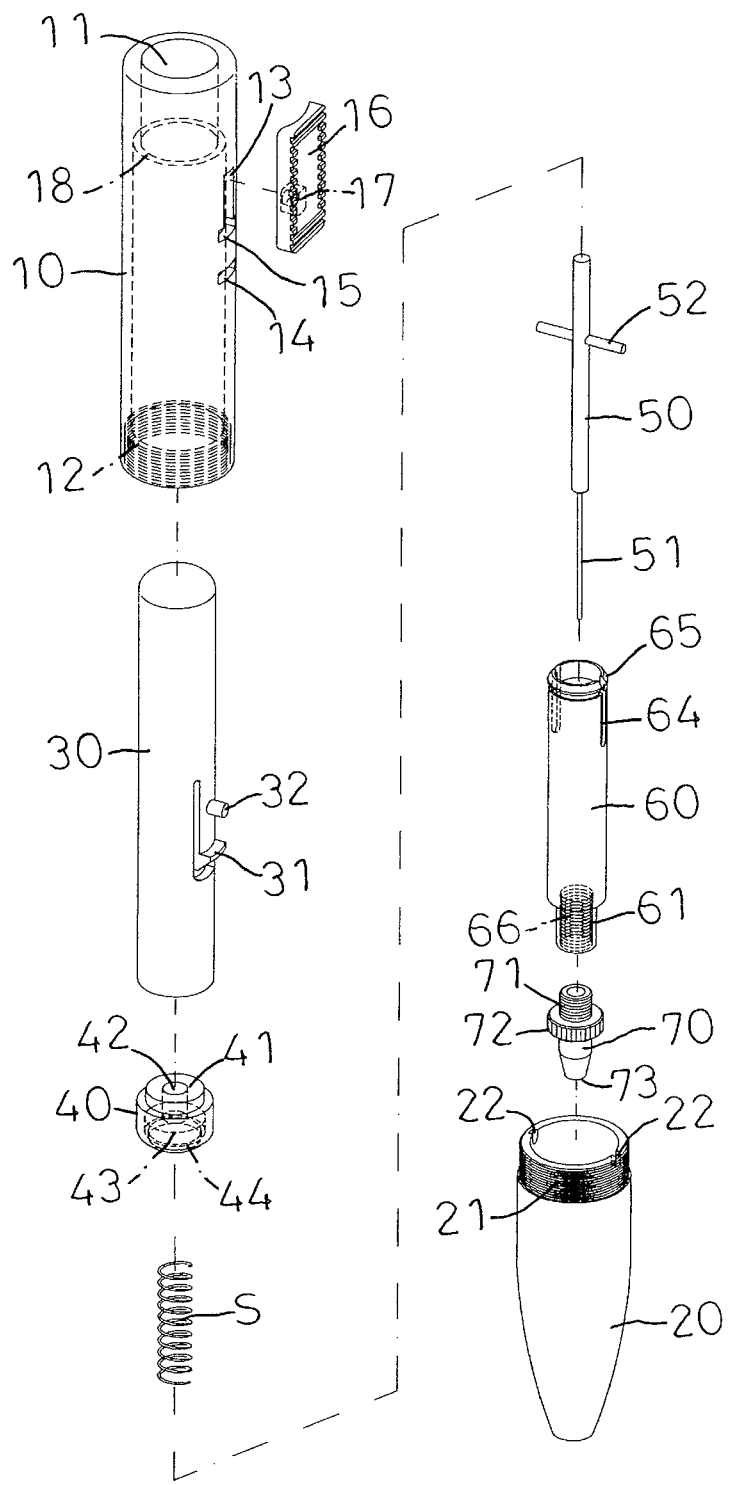
FIG. 10 is a perspective view showing the exploded components of a sampling apparatus according to a second embodiment of the present invention.
Figure 11:
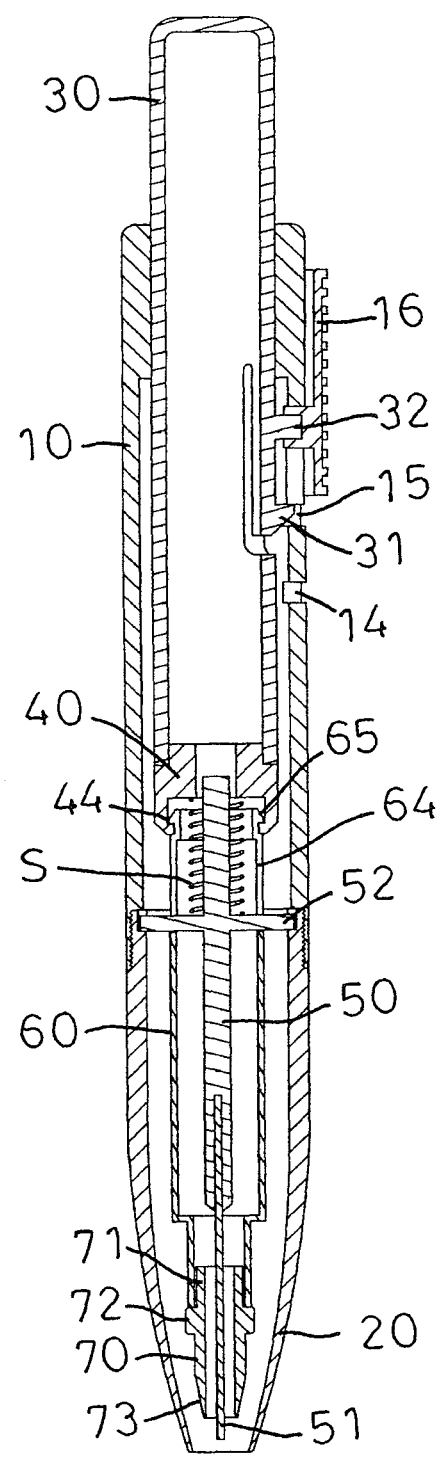
FIG. 11 is a cross sectional view showing the assembly of the sampling apparatus according to the second embodiment of the present invention.

FIG. 10 is a perspective view showing the exploded components of a sampling apparatus according to a second embodiment of the present invention. FIG. 11 is a cross sectional view showing the assembly of the sampling apparatus according to the second embodiment of the present invention. The affixing mount 61 of the movable sampling member 60 is not one piece formed with a tool 70, i.e., a tool 70 is replaceable and is an independent component, wherein the affixing mount 61 has an internal screwing section 66 defined therein, and the tool 70 has an external screwing section 71 arranged on a top end thereof to screw with the internal screwing section 66 of the affixing mount 61, wherein the tool 70 also has a raised loop 72 formed around a middle section thereof to rotate the tool 70 easily and has a blade 73 for cutting the sample.

While we have shown and described various embodiments in accordance with the present invention, it is clear to those skilled in the art that further embodiments may be made without departing from the scope of the present invention.

What is claimed is:

1. A sampling apparatus comprising: a tubular member, a pressing mechanism, a forcing member, and a movable sampling member; wherein the tubular member includes an inner thread section defined around a lower side of an inner wall of the tubular member to screw with a cylindrical member, the tubular member is hollow so as to accommodate the pressing mechanism, and the pressing mechanism includes a press member, a driving member, and a resilient element; the tubular member also includes an orifice defined on a central position of an upper of the tubular member to insert the press member, and the tubular member further includes a stepped shoulder formed around an upper side of the inner wall of the tubular member to prevent the pressing mechanism from removal; the driving member is inserted into a lower side of the press member, and the driving member includes an inserting segment formed on an upper side of the driving member and inserted into the lower side of the press member, an aperture defined on a central position of the inserting segment to insert the forcing member, a retaining slot defined below the driving member to retain with the movable sampling member, and a receiving groove formed in a lower side of the driving member to accommodate the resilient element; two ends of the resilient element abut against the driving member and the forcing member, such that the resilient element is pressed to generate an upward returning elasticity; the tubular member further includes a first fixing hole and a second fixing hole, and the press member includes an elastic hook fixed on an outer wall of the press member to alternatively hook with the first fixing hole and the second fixing hole, such that the movable sampling member extends out of or retracts into the cylindrical member;

the cylindrical member includes an outer thread section arranged around an upper side of an outer wall of the cylindrical member to screw with the inner thread section of the tubular member, and the cylindrical member also includes two opposite positioning recesses defined on a top end of the cylindrical member;

the forcing member includes a needle fixed on a bottom end of the forcing member and two opposite locating stems extending outwardly from an upper side of the forcing member to correspond to the two opposite positioning recesses of the cylindrical member, such that when the cylindrical member is locked in the tubular member, the two opposite locating stems are mounted in the two opposite positioning recesses of the cylindrical member so that the forcing member is fixed;

the movable sampling member includes a hollowly lower side, a hollow affixing mount, and a hollow tool, such that the needle of the forcing member retracts into the hollow tool, and the movable sampling member also includes a first blade arranged on a distal end of the tool to cut a sample and includes two opposite trenches defined on an upper side of the movable sampling member to correspond to the two opposite locating stems of the forcing member, such that when the movable sampling member extends outwardly or retracts inwardly, it shirks the two opposite locating stems, and when the movable sampling member retracts into the cylindrical member, the needle exposes outside the first blade to push the sample outwardly.

2. The sampling apparatus as claimed in claim 1, wherein the pressing mechanism further include a longitudinal hole arranged on the outer wall of the tubular member above the second fixing hole, and a pushing block is disposed outside the longitudinal hole, a fitting seat is arranged in the pushing block to correspond to the longitudinal hole; the press member also includes a coupling post extending outwardly from the outer wall of the press member above the elastic hook to fit into the fitting seat of the pushing block, such that when the pushing block is pressed, the elastic hook of the press member removes from the first fixing hole or the second fixing hole.

3. The sampling apparatus as claimed in claim 1, wherein the tool of the movable sampling member has an external screwing section arranged on a top end of the tool to screw with an internal screwing section of an affixing mount, a raised loop formed around a middle section of the raised loop, and a second blade for cutting the sample.

\* \* \* \* \*